US008778443B2

(12) United States Patent
Uckelmann et al.

(10) Patent No.: US 8,778,443 B2
(45) Date of Patent: Jul. 15, 2014

(54) METHOD FOR MANUFACTURING IMPLANT ABUTMENTS FOR DENTAL IMPLANTS, AND AN IMPLANT ABUTMENT FOR A DENTAL IMPLANT

(75) Inventors: Ingo Uckelmann, Bremen (DE); Helmut Laschütza, Ritterhude (DE)

(73) Assignee: BEGO Medical GmbH (DE)

( * ) Notice: Subject to any disclaimer, the term of this patent is extended or adjusted under 35 U.S.C. 154(b) by 1256 days.

(21) Appl. No.: 12/574,121

(22) Filed: Oct. 6, 2009

(65) Prior Publication Data
US 2010/0021865 A1 Jan. 28, 2010

Related U.S. Application Data

(63) Continuation of application No. 11/635,301, filed on Dec. 7, 2006, now abandoned, which is a continuation of application No. 10/818,862, filed on Apr. 5, 2004, now abandoned.

(30) Foreign Application Priority Data

Apr. 5, 2003 (DE) .................................. 103 15 563

(51) Int. Cl.
*B05D 3/00* (2006.01)
*A61K 6/04* (2006.01)
*A61C 8/00* (2006.01)

(52) U.S. Cl.
USPC ....... 427/2.26; 427/2.29; 433/201.1; 433/181

(58) Field of Classification Search
USPC ...................... 433/201.1, 181; 427/2.26, 2.29
See application file for complete search history.

(56) References Cited

U.S. PATENT DOCUMENTS

| 4,323,756 A | | 4/1982 | Brown et al. | |
| 4,661,071 A | | 4/1987 | Bell et al. | |
| 4,863,538 A | | 9/1989 | Deckard | |
| 4,988,297 A | * | 1/1991 | Lazzara et al. | ................ 433/173 |
| 5,052,929 A | * | 10/1991 | Seal | ............................. 433/173 |

(Continued)

FOREIGN PATENT DOCUMENTS

| CA | 2295896 | 7/2000 |
| DE | 19651909 | 6/1998 |

(Continued)

OTHER PUBLICATIONS

"Dental root Implants produced by the combined selective laser sintering/melting of titanium powders", NK Tolochko et al., Proc Instn Mech Engrs, vol. 216, Part L: J Materials: Design and Applications, pp. 267-270, Mar. 28, 2002.

(Continued)

*Primary Examiner* — Cachet Sellman
(74) *Attorney, Agent, or Firm* — Altera Law Group, LLC

(57) ABSTRACT

The invention relates to a method for manufacturing implant abutments 9 for dental implants 1, wherein the implant abutment 9 comprises a prefabricated base member 8 for joining the implant abutment to the dental implant 1, and a customized main body 15. The aim of the invention is to simplify this method of manufacturing. To this end, the main body 15 is formed by sintering and/or melting powdery material onto the base member 8 using laser sintering and/or laser melting. The invention relates also to an implant abutment manufactured by such a method.

15 Claims, 3 Drawing Sheets

(56) References Cited

U.S. PATENT DOCUMENTS

| | | |
|---|---|---|
| 5,453,007 A | 9/1995 | Wagher |
| 5,674,069 A | 10/1997 | Osorio |
| 5,716,215 A | 2/1998 | Blacklock |
| 5,768,134 A * | 6/1998 | Swaelens et al. ............ 700/121 |
| 5,873,721 A * | 2/1999 | Willoughby .................. 433/173 |
| 6,042,774 A | 3/2000 | Wilkening et al. |
| 6,048,203 A | 4/2000 | Rosenberg |
| 6,402,517 B1 * | 6/2002 | Hozumi et al. ............ 433/201.1 |
| 2002/0187458 A1 | 12/2002 | Dolabdjian et al. |
| 2003/0003420 A1 | 1/2003 | Striezel |
| 2003/0028278 A1 | 2/2003 | Darrah et al. |
| 2003/0205851 A1 | 11/2003 | Laschutza et al. |
| 2004/0031780 A1 | 2/2004 | Hagemeister et al. |

FOREIGN PATENT DOCUMENTS

| | | |
|---|---|---|
| DE | 199 01 643 A1 | 7/2000 |
| DE | 100 52 389 A1 | 5/2002 |
| DE | 102 31 136 A1 | 2/2003 |
| EP | 0734842 | 10/1996 |
| EP | 0904743 | 3/1999 |
| EP | 0966927 | 12/1999 |
| EP | 1021997 | 7/2000 |
| EP | 1199050 | 4/2002 |
| EP | 1269934 | 1/2003 |
| GB | 2378151 | 2/2003 |

OTHER PUBLICATIONS

Free Form Fabrication of Metallic Components Using Laser Engineered Net Shaping (Lens™), M.L. Griffith et al., paper presented at the Solid Free Form Fabrication Symposium, Austin, Texas, Aug. 12-14, 1996.

"Schneller Zahn aus Titan", Lasertechnik, Fraunhofer Magazin, pp. 32, Apr. 2002.

"Direktes Selektives Laser Sintern einkomponentiger metallischer Werkoffe", Wilhelm Meiners, Apr. 15, 1999.

* cited by examiner

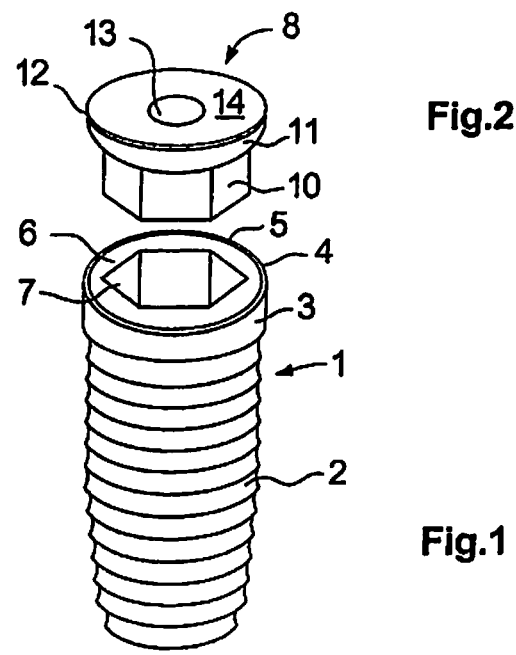
Fig.2
Fig.1
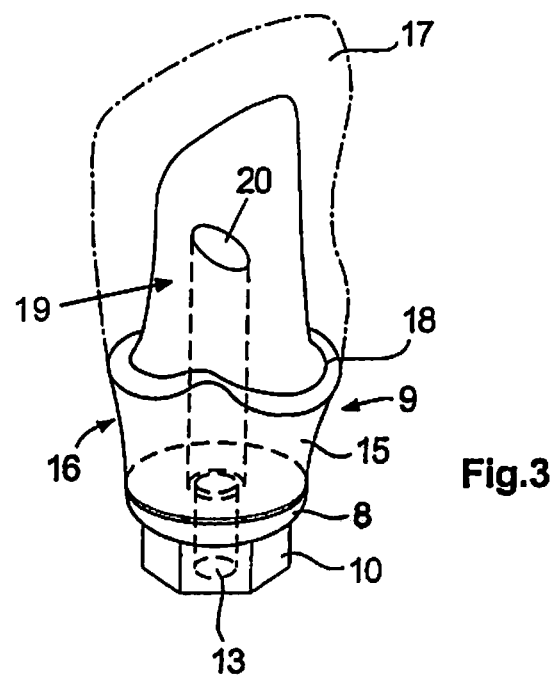
Fig.3

METHOD FOR MANUFACTURING IMPLANT ABUTMENTS FOR DENTAL IMPLANTS, AND AN IMPLANT ABUTMENT FOR A DENTAL IMPLANT

CROSS-REFERENCE TO RELATED APPLICATION

This application is a continuation of application Ser. No. 11/635,301, filed 7 Dec. 2006 now abandoned which is a continuation application Ser. No. 10/818,862 now abandoned. The application is incorporated herein by reference.

BACKGROUND OF THE INVENTION

The invention relates to a method for manufacturing implant abutments for dental implants, wherein the implant abutment comprises a prefabricated base member for joining the implant abutment to the dental implant, and a customized main body.

The invention also relates to an implant abutment for a dental implant, said abutment comprising a prefabricated base member for joining the implant abutment to the dental implant, and a customized main body.

In the field of dental technology, dental implants onto which implant abutments are attached are used to replace natural teeth. An implant abutment typically comprises a base member for joining the implant abutment to the dental implant and a main body that is customized to the tooth being replaced, to the remaining teeth and/or to the specific details of the jawbone. However, the main body does not form the visible area of the implanted tooth. The main body itself is surrounded instead by a crown.

Implant abutments of this kind are conventionally manufactured by modeling, on a standard base member, a wax model that is substantially identical to the subsequent main body. A mold is produced from said wax model. The wax is then melted in a furnace to produce a negative mold of the main body. Said negative mold is then melted out with suitable material, such as gold alloys or alloys that do not contain precious metals. During this process, the prefabricated base member is melted onto the main body and thus fixedly attached thereto. An implant abutment is thereby produced that generally requires manual finishing.

This process of making implant abutments is laborious and requires much manual work, in particular. It is therefore costly.

BRIEF SUMMARY OF THE INVENTION

The invention is therefore based on the technical problem of simplifying the production of implant abutments.

The invention solves this problem by means of a method of the kind initially specified, in which the main body is formed by sintering and/or melting powdery material onto the base member using laser sintering and/or laser melting.

The invention further solves the problem, for an implant abutment of the kind initially specified, in that the main body is formed by sintering and/or melting powdery material layer by layer using laser sintering and/or laser melting.

This method of manufacturing dental implant abutments has the advantage of being able to use a prefabricated base member that can be made in large quantities and therefore with a production process that optimizes quality and cost. Such a prefabricated base member therefore exhibits a high level of precision and is also relatively inexpensive. A high level of precision is advantageous in that the base member is a connector for attaching the dental implant to the implant abutment and should be capable of being fitted into the implant in a defined position and substantially without clearance. Such a high level of precision can be achieved in an automated manufacturing process, in particular. However, automation is efficient only if a large quantity of identical components are being made. For this reason, it is particularly advantageous to use prefabricated, standardized base members.

Production of the main body using laser sintering and/or laser melting permits extensively automated production of the implant abutment, since a computer-aided laser is able to generate predefined shapes. The predefined forms are firstly determined with the help of a computer. Data obtained by scanning the patient's dentures or a dental cast of the patient's dentures are used as a basis for determining the optimal form of the implant abutment.

Another reason why the laser sintering and/or laser melting method is particularly advantageous is that this method allows complex structures of virtually any shape and size to be produced.

Furthermore, it is usually not necessary to perform subsequent finishing work on implant abutments formed in this way.

Another advantage of laser sintering and laser melting is that the material comprising the main body can be easily applied, i.e. sintered or melted, onto the base member without subsequent melting, bonding or cementing being necessary. Instead, the base member is covered directly with the respective material. The first layer is applied directly onto the base member. The second and subsequent layers are then applied onto the previously applied layer.

This method can therefore be automated to a large extent. There is little or no need for any manual operations. The invention thus permits the inexpensive production of precision implant abutments.

Computer-aided production of implant abutments also makes it possible to simplify the production of crowns that are subsequently attached to the abutment, since the preparation cast of the implant abutment is similarly determined and created by computer-aided means. The data used to make the implant abutment can also be used to make the crown, whereupon the production process for the entire artificial tooth comprising an implant, implant abutment and crown is further simplified.

Titanium in pulverized form, or a powder containing titanium, or a pulverized titanium alloy is preferred as material. Said material is particularly suitable, since it is chemically stable and does not interact with the human organism.

A particularly preferred embodiment is one in which the main body, i.e. the sintered or melted material, is subsequently given a ceramic coating. The ceramic coating is advantageously applied by means of electrophoresis, or again by laser sintering. The implant abutment is coated also, so it is possible to optimize the esthetic appearance of the implant abutment. Coating prevents dark materials such as titanium, for example, showing through the crown attached onto the main body, since the main body itself is no longer dark-colored, but ceramic-colored instead. Ceramic material can similarly be applied at the transition between implant and crown, so that no dark edges occur at the gingival margin as a result of titanium material showing through the gum.

The esthetic appearance of the implant abutment is therefore considerably improved by means of this ceramic coating.

The ceramic coating has the further advantage that the surface characteristics of the implant abutment are also improved where there is surrounding tissue. This improves contact with the gum and reduces the risk of a gap forming between the two, since the gum has better contact with a ceramic surface than with a titanium surface.

However, it is particularly preferred to mask the base member from any ceramic coating. This is advantageous because the base member is generally inserted completely into the implant. This keeps the contact surfaces between the implant and the base member of the implant abutment free of any ceramic coating. This avoids the precision fit of the base member and the implant from being impaired by any ceramic coating in this area.

BRIEF DESCRIPTION OF THE SEVERAL VIEWS OF THE DRAWINGS

Other advantageous embodiments are characterized in the subclaims, and in the embodiments explained with reference to the enclosed drawings. The drawings show:

FIG. 1 a dental implant;

FIG. 2 a base member for an implant abutment according to the invention;

FIG. 3 a possible embodiment of an implant abutment according to the invention, comprising a base member pursuant to FIG. 2 and a main body attached onto it;

DETAILED DESCRIPTION OF THE INVENTION

Figure 4:
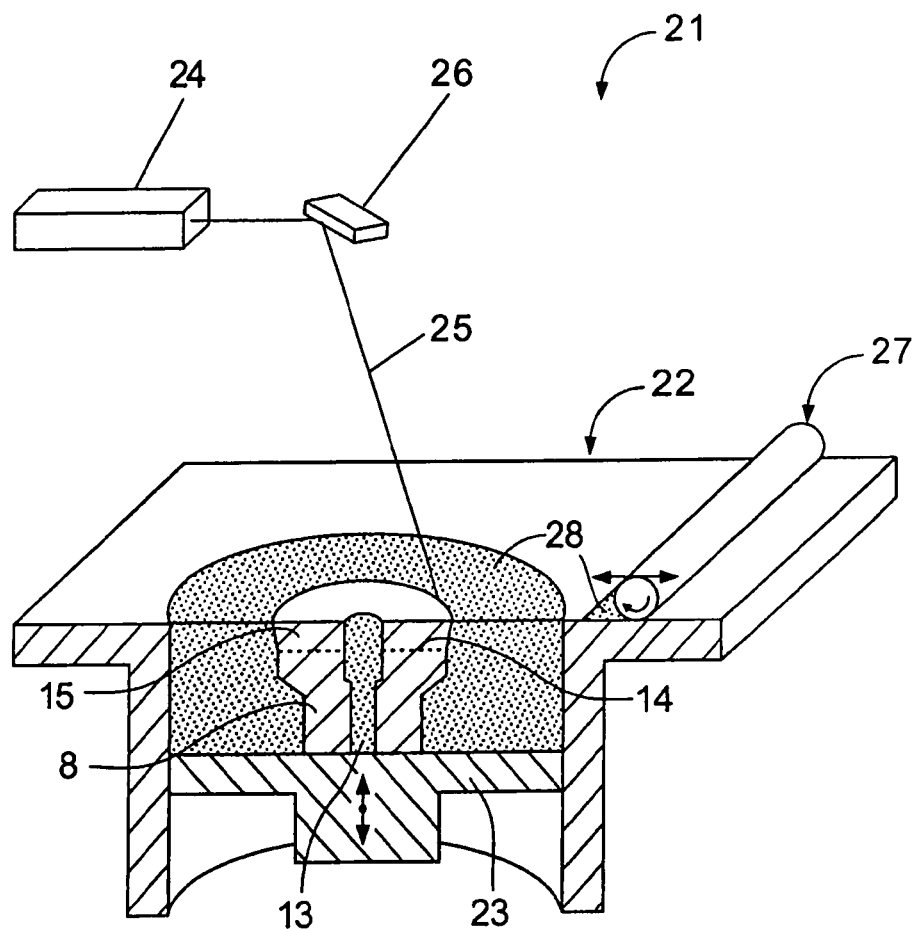
FIG. 4 a device for performing the method according to the invention.

FIG. 1 shows a dental implant 1 with an outer thread 2 that may be configured as a self-cutting outer thread, for example. In an upper unthreaded portion 3, dental implant 1 has a generally cylindrical outer contour. Said upper portion 3 changes at upper edge 4 into a circular plane surface 5. Said circular plane surface 5 changes toward the inside of implant 1 into a conical plane surface 6. Said conical plane surface 6 is configured like a funnel and ends in a recess 7 like a hexagon socket.

At the lower end of recess 7 there is a through bore (not shown) disposed concentrically to implant 1 and having an internal thread for receiving an screw fastener for fastening an implant abutment, described below, to implant 1.

FIG. 2 shows a base member 8 of an implant abutment 9 as shown in FIG. 3. The base member 8 has an outer hexagon 10 that can be inserted substantially without clearance into the hexagon socket-like recess 7. In this way, the base member 8 can be attached with positive engagement to implant 1 such that it cannot be rotated. The base member 8 thus serves as a connector element for joining the implant abutment 9 to the implant 1.

In an alternative embodiment, a different type of fit is provided instead of the outer hexagon 10 and recess 7 like a hexagon socket, for example a triangular, square or other polyhedral structure that ensures the implant abutment 9 is attached to implant 1 in such a way that it cannot twist or rotate.

The base member 8 has an adjacent conical portion 11, the diameter of said conical portion 11 increasing with greater distance from the outer hexagon. The maximum diameter of conical portion 11 is reached at the upper portion of base member 8, whereby conical portion 11 changes in said upper portion into a cylindrical portion 12. This maximum diameter of base member 8 is substantially identical to the outer diameter of upper portion 3 of implant 1. Owing to the circular surface 5 at the upper end of implant 1, the conical portion 6 of implant 1 is essentially completely closed and sealed when the implant abutment is mounted.

The base member 8 also has an axial through bore 13 that is aligned coaxially with the through bore inside implant 1.

In its upper portion facing away from implant 1, through bore 13 has a larger diameter than in its lower portion facing implant 1. The larger diameter serves to receive a screw head of the fastening screw for fastening the base member 8 to implant 1. The transition between the portion where through bore 13 has a larger diameter to the portion where through bore 13 has a smaller diameter serves as a support for the screw.

Implant 1 and base member 8 are preferably made of titanium or a titanium alloy. Base member 8 and/or implant 1 are preferably CNC-milled, which ensures that these parts are of high precision. However, they may also be cast and then finished if necessary.

The upper end of base member 8 is demarcated by a plane surface 14 onto which the additional material, such as pulverized titanium or a pulverized titanium alloy, is sintered and/or melted.

FIG. 3 shows the implant abutment with such material applied to the base member 8 to form a main body 15 of the implant abutment 9. Said main body 15 is customized to the particular specifications of the artificially produced tooth. A lower portion 16 of the main body 15 forms a transitional portion between implant 1 and a crown 17 (shown with a chain-dotted line) for mounting onto implant abutment 9. At the upper end of the transitional portion 16, a preparation edge 18 is provided onto which the crown 17 is mounted. Above the preparation edge 18, the main body 15 changes to a preparation portion 19, i.e. a portion onto which the crown 17 is fastened.

The through bore 13 of base member 8 continues as a cylindrical recess in main body 15 and ends in an upper opening 20 for receiving the aforementioned fastening screw.

An artificial tooth is fastened in the jaw as follows: first, a hole is drilled in the jaw. Implant 1 is then screwed into said hole. Finally (after prior healing), the implant abutment 9 is attached to the implant 1 by means of the base member 8, which serves as a connector. A fastening screw is inserted into the implant abutment 9 through opening 20 and fastened to the implant 1. The crown 17 is then mounted on the implant abutment 9 and cemented or bonded thereto.

FIG. 4 shows a device 21 for laser sintering or laser melting. Device 21 has a table 22 with a vertically adjustable platform 23 that can be vertically adjusted stepwise, for example in steps of 0.05-0.2 mm, by a drive means that is not shown.

Device 21 also has a laser 24 disposed above table 22, for example a $CO_2$ laser, beam 25 of which is guided through a suitable device, for example a computer-controlled reflecting galvanometer 26.

Device 21 also has a coating mechanism 27 by means of which powdery material 28 is uniformly distributed over the surface of table 22, such that the space between the surface of platform 23 and the surface of table 22 is filled with powdery material 28.

An implant abutment is now made in the following way: at first, platform 23 is in an upper initial setting. The base member 8 is positioned on platform 23 in such a way that the substantially plane surface 14 of the upper portion is aligned in the same plane as the surface of table 22. The area around the base member 8, between platform 23 and the surface of table 22, is then filled with powdery material.

A lay of powdery material us then applied over the surface of base member 8 using the coating mechanism 27. There is now a thin layer of the powdery material, for example with a thickness of 0.05-0.2 mm, above base member 8.

Laser 24 is then activated and its laser beam 25 directed onto said layer of powdery material covering the surface 14 of base member 8. Owing to the heat it generates, the laser beam 25 solidifies or melts the powdery material, which is then either sintered onto the base member 8 or completely fused with the base member 8, depending on the amount of energy applied to the powdery material. In accordance with the pre-programmed shape of the implant abutment 9, laser beam 25 travels up and down the surface 14 of base member 8, onto which a layer is to be applied, as well as any adjacent or non-adjacent areas. The layer thus applied is not necessarily perfectly congruent with the shape of the surface of base member 8. In particular, it may be larger or smaller, and leave out certain portions such as the portion around the through bore 13, or create new portions. In this way, a first layer of the initially powdery material is sintered or melted onto base member 8.

The laser is then deactivated and platform 23 is lowered by one layer, e.g. by 0.05-0.2 mm. Using the coating mechanism 27, a new layer of powdery materials 28 is applied and smoothed. Laser 24 is then reactivated, and the computer-controlled laser beam 25 again scans the area within which the powdery material 28 is to be fused or sintered with the previously applied layer, as well as adjacent or non-adjacent areas if necessary. This process of applying layers of powdery material and then sintering or fusing said layers with the base member 8 and/or previously applied layers using a laser 24 is performed repeatedly until the desired shape of implant abutment 9 has been formed on the base member 8 of main body 15.

By means of this method, any desired shape of implant abutment can be formed, with recesses anywhere that may be desired. In particular, the through bore 13 in the base member can be continued as a recess in the main body 15, also with different cross-sectional shapes if so desired.

This method is particularly suitable in that complex geometries of implant abutments can be easily produced. In principle, any material can be sintered using laser beam 25. However, titanium powder, powder containing titanium, or a pulverized titanium alloy are particularly suitable.

The implant abutment 9 manufactured in this way is subsequently coated with a ceramic, preferably only in the main body portion 15, i.e. base member 8 is left out of such ceramic coating. Ceramic coating is preferably performed using electrophoresis. Alternatively or additionally, however, the ceramic coating can be applied using laser sintering. A device such as that shown in FIG. 4 can be used for this purpose. A ceramic material would then be used for the powdery material. However, the laser beam 25 is then guided in such a way that the laser beam 25 can scan the outer surface of the implant abutment 9, and in any case the surface of the main body 15. It may be necessary to this end to move the reflecting galvanometer 26, in particular in a plane parallel to the surface of table 22. Additionally or alternatively, the laser sintering device may also be configured in such a way that table 22 is rotatable.

Figure 5:
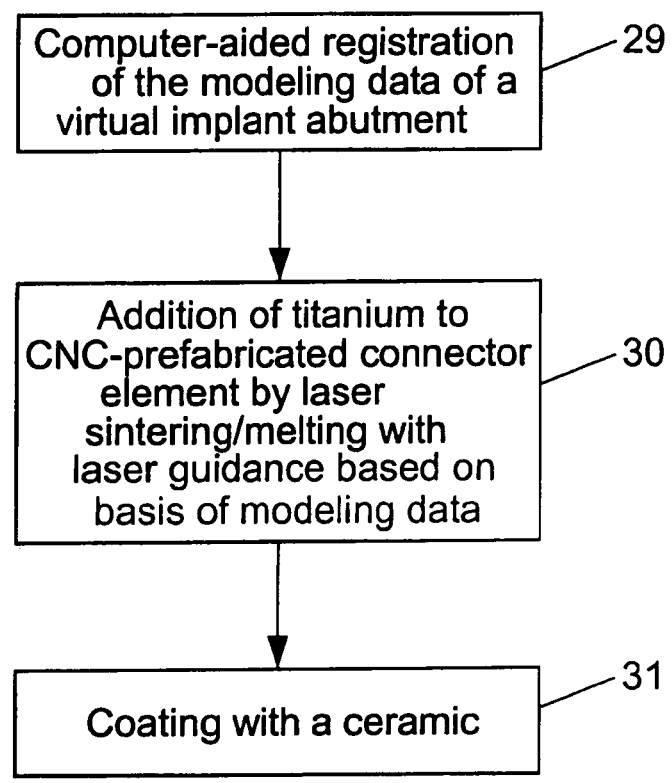
FIG. 5 a schematic flow diagram of an embodiment of the method according to the invention.

FIG. 5 illustrates basic steps of the method for manufacturing implant abutments according to a preferred embodiment of the invention. In a first step 29, a model of a virtual implant abutment is generated. The model data obtained by this means are subsequently used to guide the laser beam 25, in particular to control the reflecting galvanometer 26.

In a second step 39 following the first step 29, and using the aforesaid model data, titanium is applied to a CNC-prefabricated connector element (base member 8) by laser sintering and/or laser melting.

In a further step 31, the implant abutment made in this way is coated with ceramic material.

Thanks to the invention, customized, tooth-colored implant abutments with optimized preparation and transition forms can be manufactured. They permit simpler prosthetics, excellent esthetics and an optimized surface layer of the implant abutment for contact with surrounding tissue.

The invention claimed is:

1. A method for manufacturing implant abutments for dental implants, wherein the implant abutment comprises a prefabricated base member for joining the implant abutment to the dental implant, and a customized main body,
wherein
the main body is formed by sintering and/or melting pulverized material onto the base member using laser sintering and/or laser melting,
wherein the pulverized material is titanium powder or a powder containing titanium.

2. Method according to claim 1,
wherein
a laser beam travels point by point along a layer to be sintered and/or melted.

3. A method according to claim 2,
wherein
the laser beam is guided by a control unit on the basis of previously computed model data of a virtual implant abutment.

4. Method according to claim 1,
wherein
the base member is a connector element that is independent of the specific implant abutment.

5. Method according to claim 1,
wherein
the base member is prefabricated by CNC milling.

6. Method according to claim 1,
wherein
the base member is cast.

7. Method according to claim 1,
wherein
the sintered and/or melted material is given a ceramic coating.

8. Method according to claim 7,
wherein
ceramic coating is performed by electrophoresis.

9. Method according to claim 7,
wherein
ceramic coating is performed using laser sintering.

10. Method according to claim 7,
wherein
the ceramic coating is not applied to the base member.

11. A method for manufacturing implant abutments for dental implants, wherein the implant abutment comprises a prefabricated base member for joining the implant abutment to the dental implant, and a customized main body, comprising the steps of:
a. placing the base member in a well for receiving pulverized material;
b. putting said pulverized material into said well wherein the pulverized material is titanium powder or a powder containing titanium;
c. locating a laser beam emitter above said well such that it can reach substantially all points on said base member exposed within said well; and d. building up layers of material onto said base member by melting said pulverized material onto the base member using laser melting in a succession of layers, said laser being computer controlled to melt said material in locations according to user specification.

12. A method for manufacturing implant abutments for dental implants, wherein the implant abutment comprises a prefabricated base member for joining the implant abutment to the dental implant, and a customized main body,
    wherein the base member has a plain upper surface and the main body is formed by sintering and/or melting pulverized material onto said plain upper surface of the base member using laser sintering and/or laser melting
    wherein the pulverized material is titanium powder or a powder containing titanium.

13. A method for manufacturing implant abutments for dental implants, wherein the implant abutment comprises a prefabricated base member for joining the implant abutment to the dental implant, and a customized main body,
    wherein the main body is formed by sintering and/or melting pulverized material onto the base member using laser sintering and/or laser melting, and wherein the base member is positioned on a platform such that a substantially plain surface of an upper part of the base member is positioned in a plane of a surface of a table of an apparatus for laser sintering or laser melting wherein the pulverized material is titanium powder or a powder containing titanium.

14. A method for manufacturing implant abutments for dental implants, wherein the implant abutment comprises a prefabricated base member for joining the implant abutment to the dental implant, and a customized main body,
    wherein the main body is formed by sintering and/or melting pulverized material onto the base member using laser sintering and/or laser melting;
    and wherein one data set is both used for building up the main body and for building up a crown to be attaches to the main body wherein the pulverized material is titanium powder or a powder containing titanium.

15. A method for manufacturing implant abutments for dental implants,
    wherein the implant abutment comprises a prefabricated base member for joining the implant abutment to the dental implant, and a customized main body,
    wherein
    the main body is formed by sintering and/or melting pulverized material onto the base member using laser sintering and/or laser melting,
    wherein the pulverized material is titanium powder or a powder containing titanium;
    wherein the base member is cast; wherein a laser beam travels point by point along a layer to be sintered and/or melted;
    wherein the laser beam is guided by a control unit on the basis of previously computed model data of a virtual implant abutment; and
    wherein the base member is a connector element that is independent of the specific implant abutment.

* * * * *